US00PP29850P3

(12) United States Plant Patent
Probasco et al.

(10) Patent No.: US PP29,850 P3
(45) Date of Patent: Nov. 20, 2018

(54) HOP PLANT NAMED 'HBC 682'

(50) Latin Name: *Humulus lupulus*
Varietal Denomination: HBC 682

(71) Applicants: Eugene G. Probasco, Yakima, WA (US); Jason Perrault, Toppenish, WA (US)

(72) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 15/330,746

(22) Filed: Nov. 1, 2016

(65) Prior Publication Data

US 2017/0127588 P1 May 4, 2017

Related U.S. Application Data

(60) Provisional application No. 62/285,575, filed on Nov. 2, 2015.

(51) Int. Cl.
*A01H 5/00* (2018.01)

(52) U.S. Cl.
USPC ..... Plt./236
CPC ..... *A01H 5/00* (2013.01)

(58) Field of Classification Search
USPC ..... Plt./360, 236
CPC ..... A01H 5/00
See application file for complete search history.

*Primary Examiner* — Kent L Bell
(74) *Attorney, Agent, or Firm* — Svendsen Legal, LLC

(57) ABSTRACT

A new hop plant named 'HBC 682' is disclosed. 'HBC 682' is used for its exceptional and unique aromatic qualities.

6 Drawing Sheets

Genus and species: *Humulus lupulus.*
Variety denomination: 'HBC 682'.

STATEMENT REGARDING FEDERALLY SPONSORED RESEARCH OR DEVELOPMENT

None

BACKGROUND OF THE INVENTION

'HBC 682' is a product of a controlled breeding program carried out by the inventors in the Yakima Valley of Washington State. 'HBC 682' was one of several seedlings resulting from an open pollination made in 2010 with female parent 'HBC 463' (unpatented). A single plant of 'HBC 682' was selected in 2013 and was asexually reproduced via softwood cuttings in a greenhouse near Toppenish, Wash. In 2014 'HBC 682' was expanded to 30 plants planted in the area of Toppenish, Wash., and also expanded to two multi-acre trials near Toppenish, Wash. The plants were observed and evaluated for several years. Throughout several generations of asexual propagation, 'HBC 682' has been observed to retain its distinctive characteristics and remain true to type.

COMPARISON OF 'HBC 682' TO PARENT PLANT AND COMARISON CULTIVAR

Table 1. below, sets forth some of the distinguishing characteristics of 'HBC 682' as compared to its female parent 'HBC 463', and to the 'Columbus' cultivar as a closely comparable cultivar.

TABLE 1

| | INSTANT CV. 'HBC 682' | FEMALE PARENT 'HBC 463' | COMPARISON CV. 'COLUMBUS' |
|---|---|---|---|
| Alpha (% of cone weight) | 18-22 | 16-17 | 14.5-17.5 |
| Beta (% of cone weight) | 4.5-6 | 6-7 | 4.5-6.0 |
| Co-humulone (% of alpha acids) | 28-32 | 29 | 28-30 |
| Total Oil (mL/100 g) | 1-2.5 | 2.5 | 2.5-4.5 |
| Aroma Profile | herbal, earthy, floral | not available | earthy, citrus, spicy |

BRIEF DESCRIPTION OF THE PHOTOGRAPHS

Figure 1:
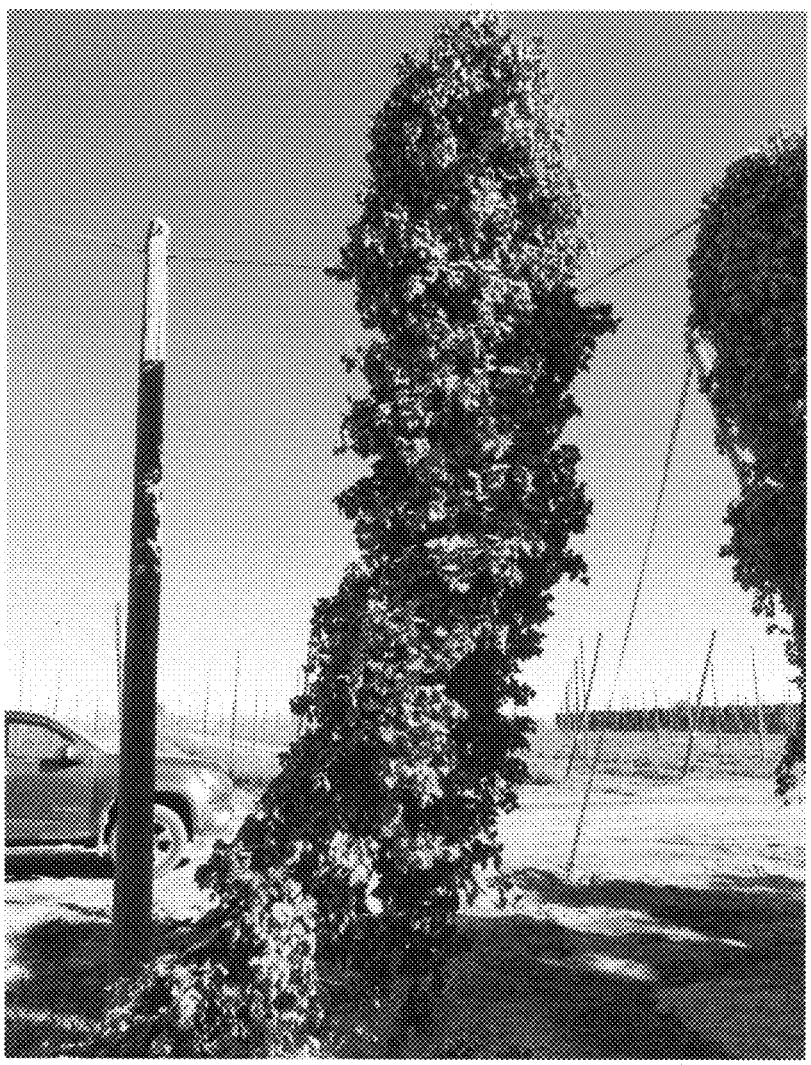
FIG. 1 illustrates a mature 'HBC 682' hop plant grown on a trellis.
Figure 2:
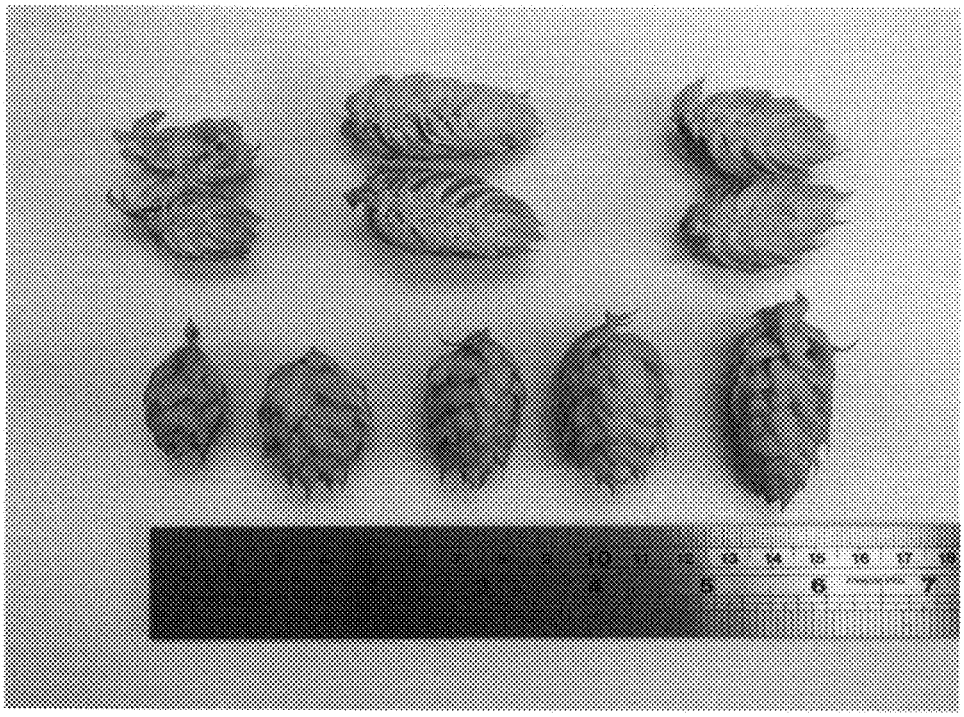
FIG. 2 illustrates whole cones and cross sections of cones of the 'HBC 682' hop plant.
Figure 3:
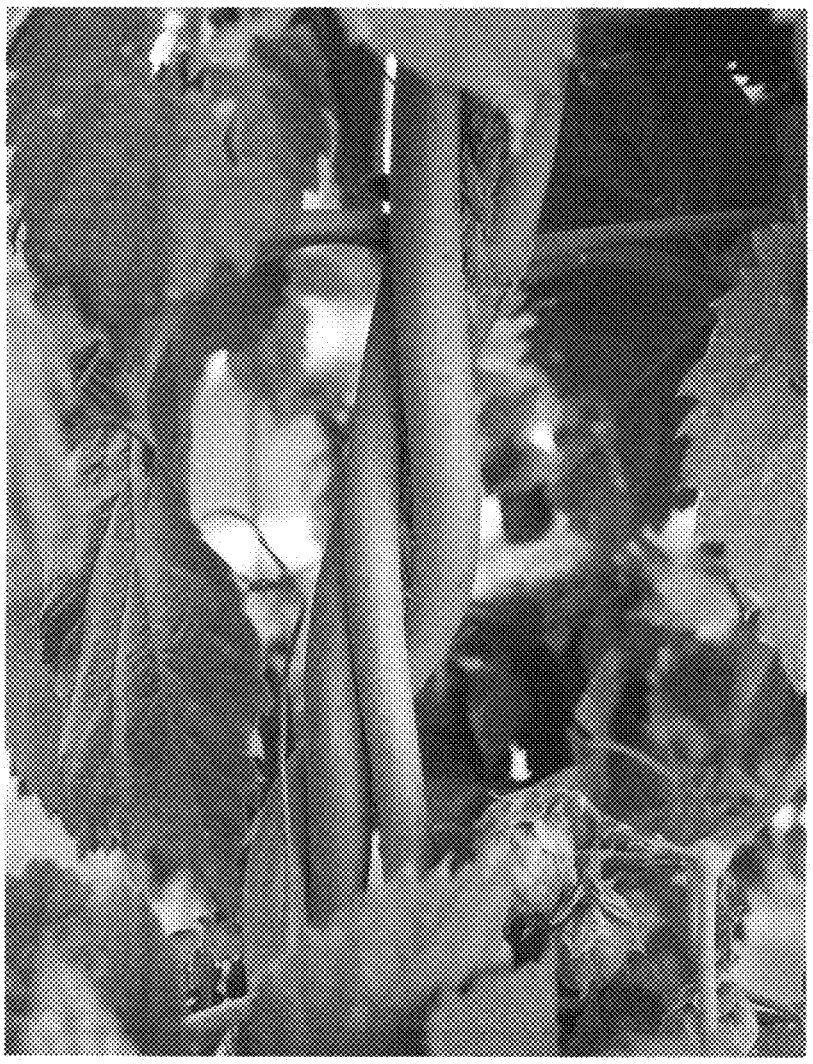
FIG. 3 illustrates the bine of a mature 'HBC 682' hop plant.
Figure 4:
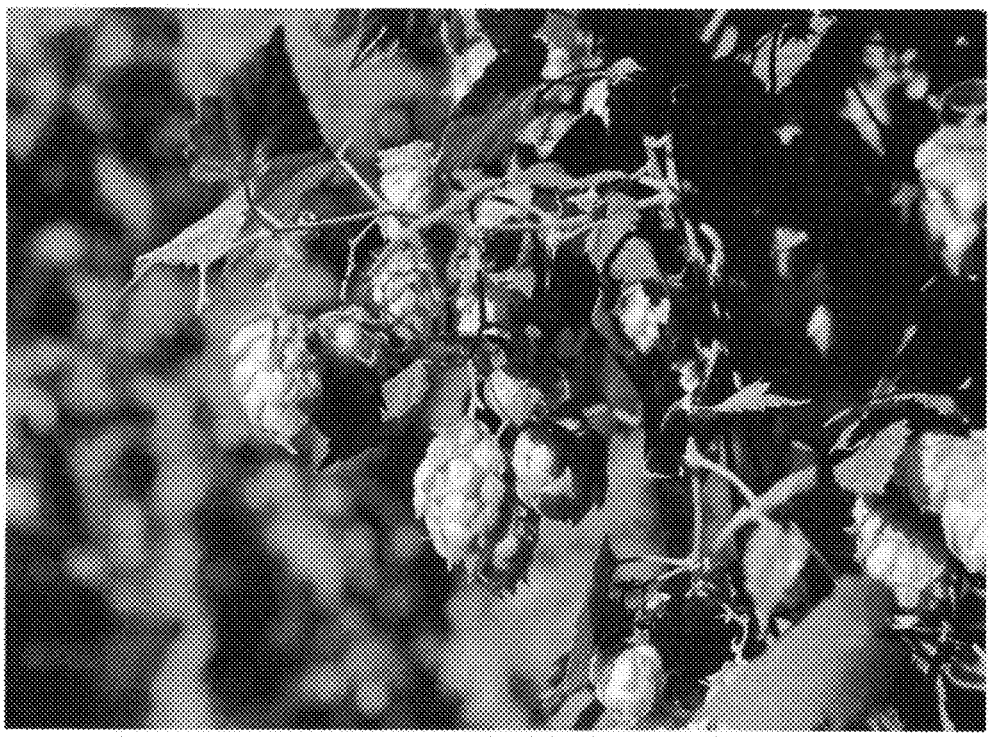
FIG. 4 illustrates cones on a mature 'HBC 682' hop plant.
Figure 5:
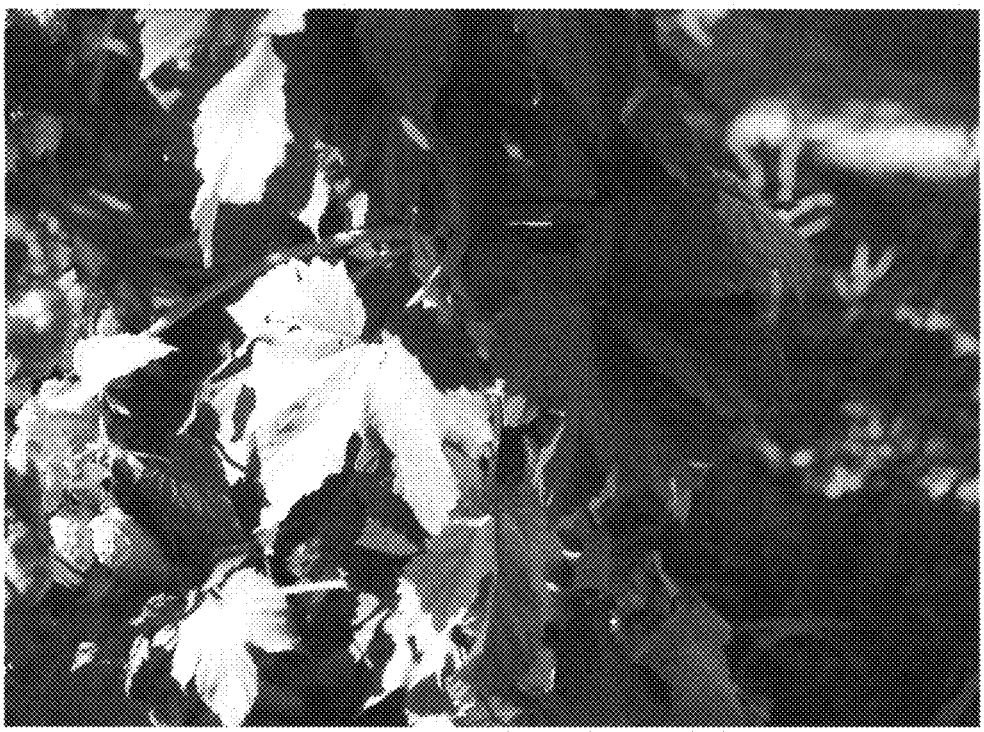
FIG. 5 illustrates leaves on a mature 'HBC 682' hop plant.
Figure 6:
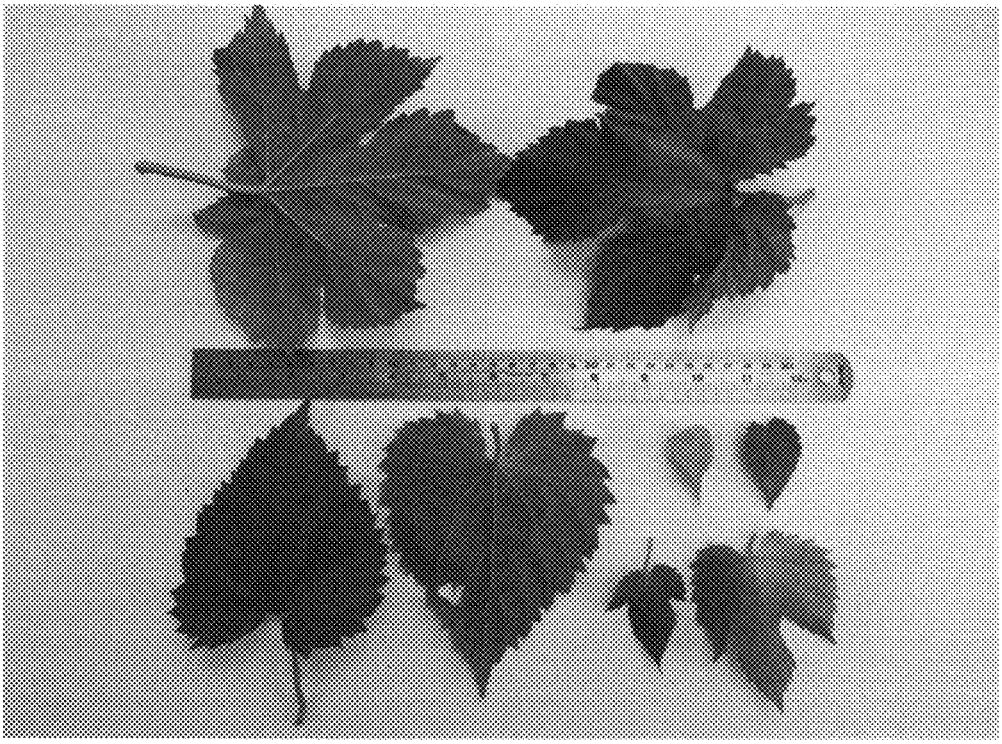
FIG. 6 illustrates leaves of the 'HBC 682' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2013-2015 growing seasons at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. All color references are based on The Royal Horticultural Society Colour Chart.

Ploidy: Diploid (2n=2x).

Sex: Female.

Disease/pest resistance/susceptibility: Resistant to powdery mildew. Reaction to other common hop diseases unknown, none observed to date.

Use: Brewing beer and ale.

Harvest date: September (during 2013 to 2015 growing seasons at Toppenish, Wash.).

Crop yield: Approximately between 2,400 lbs per acre and 3,000 lbs per acre.

Plant shape: Climbing bine, columnar growth.

Quality characteristics (averages):

*Alpha acid* (*as % of cone weight*).—18% to 22%.
*Beta acid* (*as % of cone weight*).—4.5% to 6%.
*Cohumulone* (*as % of alpha acids*).—28% to 32%.
*Storageability* (*% loss*).—20% to 30%.

Oil analytical characteristics (averages):

*Total oil* (*ml*/100 *g of cones*).—1 ml to 2.5 ml.
*A-pinene*.—0.04% Total Oil.
*B-pinene*.—0.90% Total Oil.
*Myrcene*.—36.95% Total Oil.
2-*methyl-butyl isobutyrate*.—0.09% Total Oil.
*Limonene*.—0.12% Total Oil.
*Linalool*.—0.64% Total Oil.
*Caryophyllene*.—8.44% Total Oil.
*Farnesene*.—0.52% Total Oil.
*Humulene*.—13.18% Total Oil.
*Citral*.—1.12% Total Oil.
*Geranyl acetate*.—0.16% Total Oil.
*Citronellol*.—3.36% Total Oil.
*Nerol*.—0.39% Total Oil.
*Geraniol*.—0.05% Total Oil.
*B-lonene*.—0.03% Total Oil.

Bine:

*Color*.—Green 144B.
*Stripe present*.—No.
*Stipule direction*.—Downward.
*Stipule color*.—Green 144B.
*Average number of stipule per bine*.—Two per node.
*Typical and observed bine length*.—Typical bine growth of 21 feet to 23 feet, when grown on a standard eighteen foot trellis.
*Internode length of bines*.—19 cm to 23 cm.
*Bine diameter*.—10 mm at base; 9 mm at nine feet; 9 mm at terminal end of eighteen feet.

Lateral:

*Color*.—Green 144C.
*Typical and observed lateral length*.—84 cm to 134 cm.
*Internode length of laterals*.—2.5 cm to 10.1 cm.
*Lateral diameter*.—5 mm to 7 mm at the base; and 1.5 mm to 2 mm at the terminal end.

Leaf:

*Arrangement*.—Opposite.
*Shape*.—Palmate.
*Leaf apex descriptor*.—Acuminate.
*Leaf base descriptor*.—Cordate.
*Average length of mature lea*.—10 cm.
*Average width of mature leaf*.—11 cm.
*Color of mature leaf upper surface*.—Green N134B.
*Color of mature leaf lower surface*.—About Green 137B.
*Color of immature leaf upper surface*.—Green 132A.
*Color of immature leaf lower surface*.—Green 132A.
*Number of lobes*.—3.
*Margin*.—Serrate.
*Serrations per inch*.—4.
*Average petiole length* (*mature*).—70 mm.
*Petiole color*.—Yellow-Green 145A.
*Petiole color at base*.—Yellow-Green 145A.
*Venation*.—Palmate.
*Vein color*.—Green 134B.

Cone:

*Avg. length*.—37 mm.
*Avg. diameter*.—20 mm.
*Avg. weight*.—800 mg to 1200 mg.
*Pickability*.—Good.
*Bract tip color*.—Green N134B.
*Bract inner surface color*.—Green 134B.
*Bract outer surface color*.—Green N134C.
*Bract base color*.—Green N134C.
*Bract margin*.—Entire.
*Bract base*.—Rounded.
*Bracteole color* (*both surfaces*).—Yellow-Green 145B.
*Bracteole typical length*.—15 mm to 16 mm.
*Bracteole typical width*.—8 mm to 10 mm.
*Cone shape*.—Oblong.
*Bract shape*.—Obtuse.
*Bract tip shape*.—Cuspidate.
*Bracteole shape*.—Oblong.

What is claimed:

1. A new and distinct Hop plant as illustrated and described herein.

* * * * *